(12) United States Patent
Hori et al.

(10) Patent No.: US 6,194,148 B1
(45) Date of Patent: Feb. 27, 2001

(54) METHOD FOR DETECTING A HYBRIDIZED NUCLEIC ACID MOLECULE

(75) Inventors: Kunio Hori, Hachioji; Takeo Takahashi, Tokyo; Takao Okada, Tsukuba, all of (JP)

(73) Assignee: Olympus Optical Co., Ltd., Tokyo (JP)

( * ) Notice: Subject to any disclaimer, the term of this patent is extended or adjusted under 35 U.S.C. 154(b) by 0 days.

(21) Appl. No.: 09/019,931

(22) Filed: Feb. 6, 1998

(30) Foreign Application Priority Data

Feb. 7, 1997 (JP) .................................................... 9-025219

(51) Int. Cl.$^7$ .............................. C12Q 1/68; C12P 19/34; C07H 21/02; C07H 21/04
(52) U.S. Cl. ............................ 435/6; 435/91.2; 536/23.1; 536/24.3
(58) Field of Search ...................... 435/6, 91.2; 536/23.1, 536/74.3; 935/76, 77, 78

(56) References Cited

U.S. PATENT DOCUMENTS

| | | |
|---|---|---|
| 4,734,363 | 3/1988 | Dattagupta et al. . |
| 5,270,214 | 12/1993 | Sessler et al. . |
| 5,470,707 | 11/1995 | Sasaki et al. . |
| 5,503,979 * | 4/1996 | Kramer et al. ............................ 435/6 |
| 5,601,982 * | 2/1997 | Sargent et al. ............................ 435/6 |
| 5,607,568 * | 3/1997 | Zenharusern et al. ............... 204/600 |
| 5,620,854 | 4/1997 | Holzrichter et al. . |
| 5,871,915 * | 2/1999 | Ijiro et al. ................................ 435/6 |

FOREIGN PATENT DOCUMENTS

| | | |
|---|---|---|
| 192 168 | 8/1986 | (EP) . |
| 0599337 | 6/1994 | (EP) . |
| WO 91/14788 | 10/1991 | (WO) . |

OTHER PUBLICATIONS

Engel et al., High Resolution of Native Biological Sample Surfaces using Scanning Probe Microscopy. Current Opinions in Structural Biology 7 : 279–284 (1997).*

Ganguly et al., Detection of Mismatched Bases in Double Stranded DNA by Gel Electrophoresis. Electrophoresis 16 : 1830–1835 (1995).*

Hansma et al., Atomic Force Microscopy of Single– and Double–stranded DNA. Nucleic Acids Research 20(14) : 3585–3590 (1992).*

Henderson E., Atomic Force Microscopyof Conventional and Unconventional Nucleic Acid Structures. J. of Microscopy 167(Part 1) : 77–84 (1992).*

Hu et al., Imaging of Single Extended DNA Molecules on Flat (Aminopropyl)triethoxysilane–Mica by Atomic Force Microscopy. Langmuir 12(7) : 1697–170 (1996).*

Nilsson et al., Padlock Probes: Circularizing Oligonucleotides for Localizing DNA Detection Science 265 : 2085–2088 (1988).*

Orita et al., Detection of Polymorphisms of Human DNA by Gel Electrophoresis as Single–strand Conformation Polymorpohisms. PNAS 86 : 2766–2770 (1989).*

* cited by examiner

*Primary Examiner*—Ethan Whisenant
(74) *Attorney, Agent, or Firm*—Frishauf, Holtz, Goodman, Langer & Chick, P.C.

(57) ABSTRACT

A method for detecting a target nucleic acid molecule hybridized with a nucleic acid probe, comprising the steps of: (a) hybridizing a target nucleic acid molecule having a specific sequence to be detected in a sample with a nucleic acid probe having a sequence complementary to the sequence of the nucleic acid molecule, the nucleic acid probe being selected such that the nucleic acid molecule and the probe are partially hybridized to represent a linear conformation in a hybridized region and to represent, in an non-hybridized region, a unique structure inherent to its nucleotide sequence; (b) measuring the conformation, structure and length of the nucleic acid molecule obtained in step (a); and (c) on the basis of the measurement data obtained in the step (b), detecting the nucleic acid containing both of the linear conformation and the unique structure, thereby detecting the nucleic acid molecule hybridized with the probe.

25 Claims, 4 Drawing Sheets

METHOD FOR DETECTING A HYBRIDIZED NUCLEIC ACID MOLECULE

BACKGROUND OF THE INVENTION

1. Field of the Invention

The present invention relates to a method for microscopically detecting a nucleic acid molecule hybridized with a probe.

2. Description of the Related Art

In detecting a nucleic acid having a specific sequence, use is made of a method using a probe labeled with a radioisotope or fluorescent substance, a method of measuring the activity of an enzyme immobilized onto a probe, and a method for enzymatically amplifying a specific sequence, such as in PCR (polymerase chain reaction) (see EPO192168A2, WO91/14788, U.S. Pat. No. 4,734,363 etc.). These methods include the step of amplifying signals by certain means and raise the problem that this amplification step or a preliminary step therefor is so cumbersome that a longer time is required.

In addition, in cases where a probe labeled with a radioisotope, fluorescent substance or enzyme is used, while the amplification of the desired signals is accomplished through the labeled prove which has been bound to the target sequence, noises are also amplified through the probe which has been non-specifically bonded to a solid phase carrier having a sample and the probe immobilized thereon, thereby bringing about the problem of adverse influence on detection accuracy. To prevent this problem, it is necessary to take measures such as vigorous washing after hybridization, inclusion of other DNA at the time of hybridization, etc. However, even if such measures are taken, it is not possible to prevent nonspecific binding completely, and if the concentration of the target nucleic acid molecule is low, higher noises are caused by nonspecifically bound nucleic acid molecules, which may result in failing to detect the signals from specifically bound nucleic acids. Further, because these additional procedures make the inherently complicated experimental operation further cumbersome, there is the drawback of increases in the labor and time required for the experiment. In addition, probe-labeling operation itself also requires cumbersome procedures. Further, if a radioisotope is used, there are potential problems that a place for conducting the experiment is limited, and qualification as the experimenter is required, etc.

On the other hand, if the PCR method is used for detecting DNA, it is disadvantageous that the step of enzymatically amplifying DNA needs a longer time, and further steps of fractionating DNA by gel electrophoresis etc. is required after the amplification step. Further, a spectrophotometer, fluorescence spectrophotometer or fluorescence microscope is used for detection of signals of labeled nucleic acid molecules. In these detection systems, the target nucleic acid molecule hybridized with the probe is detected by detecting the activity of the enzyme or the fluorescence of the fluorescent substance with which the probe has been labeled. Accordingly, these detection systems suffer from the problem that the specific binding between the nucleic acid probe and the target nucleic acid molecule cannot be distinguished from the nonspecific binding of the nucleic acid probe to other nucleic acids than the target nucleic acid molecule or to the solid carrier surface.

As described above, the conventional methods of detecting nucleic acid make use of a labeled nucleic acid probe, so the step of removing the unbound nucleic acid probe by washing is required to eliminate background noises from data at the time of measurement. Further, the subject to be detected by labeling is the presence of the labeled substance itself, but not the binding itself of the probe to the target nucleic acid molecule. Therefore, there is no means of distinguishing noises caused by nonspecific binding from the signal of specific binding. As a result, if the concentration of the target nucleic acid molecule is low, noises caused by nonspecific binding are higher than the signal from specific binding, which may lead to the erroneous conclusion that the target nucleic acid molecule is not present in the sample. On the other hand, if the nonspecifically bound nucleic acid probe remains due to insufficient washing, the conclusion that the target molecule is present in the sample may be derived although the target nucleic acid is not actually present. Furthermore, because this nonspecific binding cannot be eliminated completely, it cannot be determined whether the signals detected are due to an increase in nonspecific binding resulting from insufficient washing etc. or due to specific binding when the signals are slightly higher than noises caused by nonspecific binding. Thus, such signals are considered as pseudo-positive data and it cannot be determined, in some cases, whether these data are inherently positive or negative.

SUMMARY OF THE INVENTION

Accordingly, an object of the present invention is to clearly distinguish, without confusion, specific binding of a probe to a target nucleic acid from a nonspecific one by means of directly detecting a target nucleic acid molecule hybridized with the probe without using any label. Another object of the present invention is to easily detect a nucleic acid molecule without removing unbound components by washing etc. A further object of the present invention is to detect a target nucleic acid molecule accurately in a short time.

These objects can be attained by a method for detecting a target nucleic acid molecule hybridized with a nucleic acid probe, comprising the steps of:

(a) hybridizing a target nucleic acid molecule having a specific sequence to be detected in a sample with a nucleic acid probe having a sequence complementary to the sequence of the nucleic acid molecule, the nucleic acid probe being selected such that the nucleic acid molecule and the probe are partially hybridized to represent a linear conformation in a hybridized region and to represent, in an non-hybridized region, a unique structure inherent to its nucleotide sequence;

(b) measuring the conformation, structure and length of the nucleic acid molecule obtained in step (a); and (c) on the basis of the measurement data obtained in the step (b), detecting the nucleic acid containing both of the linear conformation and the unique structure, thereby detecting the nucleic acid molecule hybridized with the probe.

In the present invention, the nucleic acid probe may be longer or shorter than or equal to the target nucleic acid molecule to be detected, insofar as a hybrid nucleic acid having a linear double-stranded portion and a folded single-stranded portion is formed upon hybridization of the probe with the target nucleic acid molecule. Further, two or more probes hybridizing with different regions in the target nucleic acid molecule can also be used.

The term "linear" used in the present invention does not mean that a nucleic acid molecule is straight shape but means that a nucleic acid is extending without folding. In general, the hybridized or renatured nucleic acid molecule has a linear conformation in nature.

The term "unique structure inherent to its nucleotide sequence" used herein is based on the finding that single-stranded nucleic acid has an "unnatural conformation", i.e., a unique structure depending on its nucleotide sequence. Such a unique structure includes, but is not limited to, at least one horn-like portion folded at least one portion, a hook-like portion, a site that seems looped when viewed in at least one direction, or a globular-like portion such as a three-dimensional polyhedral, globular or amorphous mass.

Normally, the hybridized double-stranded nucleic acid is "linear" as described above and does not show such a unique structure as that of single-stranded nucleic acid. However, it is not almost straight or absolutely straight but is gradually distorted as a whole. On the other hand, the single-stranded portion having a "unique structure inherent to its nucleotide sequence" may have an almost straight or absolutely straight portion.

Once the nucleotide sequence is determined, the conformation of its high-order structure can be defined according to its sequence and length. Accordingly, as criteria for judgement in the method of the present invention, the expected high-order structure of a single-stranded portion in a hybrid nucleic acid to be formed can be provided beforehand, based on the nucleotide sequences of both the target nucleic molecule in the sample and the nucleic acid probe. When software containing such criteria input therein is employed, automatic detection is made feasible by conducting data analysis of a microscopic image of the hybridized nucleic acid. Further, the operator who observed it under a microscope can make a judgement by using a list of the criteria.

BRIEF DESCRIPTION OF THE DRAWINGS

FIGS. 9 (a) to (g) are schematic drawings showing differences in the shapes/conformations of hybrid complexes formed upon hybridization of the same nucleic acid molecule with different probes.

DETAILED DESCRIPTION OF THE PREFERRED EMBODIMENT

Hereinafter, embodiments for carrying out the present invention will be described in the cases of using DNA samples and DNA probes. However, it would be obvious to those skilled in the art that these embodiments are only illustrative of the present invention and are not intended to limit the present invention. Any method according to the present invention is based on the observation of individual nucleic acid molecules themselves by scanning probe microscopy (SPM), rather than the properties of an aggregate of molecules as a whole. Here, scanning probe microscopy is a general term of scanning microscopy capable of observation at atomic level, including scanning tunneling microscopy (STM) and atomic force microscopy (AFM). AFM is roughly classified into three types, i.e., repulsion force type, attraction type and tapping type ("tapping type" is a registered trademark, available from Digital Instrument Ltd., Santa Barbara, Calif., USA). However, the study in this field is now being rapidly developed, and new microscopy such as frictional force microscopy, Maxwell stress microscopy, magnetic force microscopy, photon scanning tunneling microscopy, photon scanning tunneling microscopy, near-field optical microscope (SNOM) etc. is now being developed. In view of the aim of the present invention, the scanning probe microscopy in the present invention is not limited to conventional microscope such as commercially available or known microscopes which may be used singly or in combination thereof, but includes any microscopy which may be developed in the future so long as the future microscopy has resolution power at atomic level. For techniques on STM, reference can be made of e.g., the literatures (G. Binning et al., IBM J. RES. DEVELP., 30(4); 355–369, 1986; Conrad Schneiker et al., J. of Microscopy, 152(2); 585–596, 1988; and H. Kaisuka, Rev. Sci. Instrum., 60(10); 3119–3122, 1989). For techniques on AFM, reference can be made of the literatures (G. Binnig et al., Physical Review Letters, 56(9); 930–933, 1986; T. R. Albrecht et al., J. Appl. Phys., 62(7); 2599–2602, 1987; A. L. Weisenhorn et al., Appl. Phys. Lett, 54(26); 2651–2653, 1989; T. R. Alblecht et al., J. Vac. Sci. Technol., A8(4); 3386–3396, 1990; and R. C. Barrett et al., Rev. Sci. Instrum., 62(6), 1991). For techniques on SNOM, reference can be made of e.g. the literatures (Pohl et al., J. of Microscopy, 152(3); 853–861, 1988; Constant A. J. Putman, et al., Appl. Phys. Lett., 64(18); 2454–2456, 1994; and N. F. van Hulst, Appl. Phys. Lett., 62(5); 461–463, 1993). As an example of a combination of various kinds of microscopy, techniques using both STM and AFM are reported in e.g., the literature (P. S. Bryant et al., J. of Microscopy, 152(3); 871–875). Reference techniques for measuring and making an image of biological materials by these SPM techniques are described in the literatures (Zasadzinski et al., Science, 239; 1013–1015, 1988; Emch et al., J of Microscopy, 152(1); 85–92, 1988; Marti et al., J. of Microscopy, 152(3); 803–809, 1988; Drake et al., Science, 243; 1586–1589, 1989; Gould et al., J. Vac. Sci. Technol., 8(1); 369–373, 1990; Jericho et al., J. Vac. Sci. Technol., 8(1); 661–666, 1990; Coragtger et al., Micron, 25(4); 311–315, 1995). Further, reference techniques for measuring nucleic acid molecules by the SPM techniques are described in the literatures (Feng et al., J. of Microscopy, 152(3); 811–816, 1988; Driscoll et al., Nature, 346; 294–296, 1990; Firtel and Beveridge, Micron, 26(4), 347–362, 1995; Yang and Shao, Micron, 26(1); 35–49, 1995; and Rivetti et al., J. Mol. Biol., 264; 919–932, 1996). Detailed operational techniques of SPM applied to the method of the present invention can be referred to suitably in the above literatures.

Figure 1A:
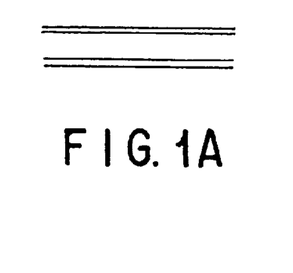
FIGS. 1A to 1C are schematic drawings showing that the conformation of a nucleic molecule is varied depending on a difference in the state of the molecule.
Figure 1B:
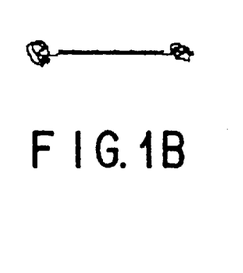
Figure 1C:
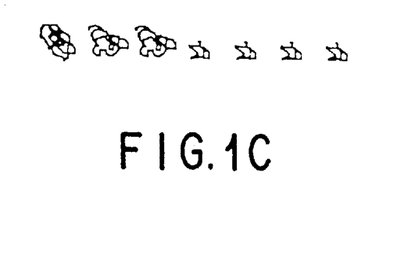

FIGS. 1A to 1C are schematic drawings showing the relationship between the state of a nucleic acid (FIG. 1A, double-stranded; FIG. 1B, partially double-stranded; and FIG. 1C, single-stranded) and its conformation. The features of the present invention are described in comparison with the prior art by reference to FIGS. 1A to 1C. FIG. 1A shows the linear conformation of a double-stranded nucleic acid (DNA) present in a sample. On the other hand, the conformation of a single-stranded nucleic acid has a three-dimensional, complicated structure formed via intramolecular bonds, which is varied depending on its sequence. Although it has been known and studied for long time that a single-stranded RNA has such a high-order structure or single strand conformation polymorphism depending on its sequence, the study on the high-order structure of DNA is relatively new (Orita, M. et al., Proc. Natl. Acac. Sci. USA, 86; 2766–2770 (1989); Orita, M. et al., Genomics, 5; 874–879 (1989)). Orita et al. have separated a plurality of single-stranded DNAs having different nucleotide sequences according to the differences in conformation of the respective nucleotide sequences by means of gel electrophoresis, thereafter, immobilized the separated DNAs onto a nylon membrane, and hybridized them with a DNA probe and RNA probe labeled with different radioisotopes, thereby detecting individual single-stranded DNAs.

However, there is no report on the hybridization of an unlabeled DNA probe (or RNA probe) with single-stranded DNA (or RNA) as shown in the present invention. Further, there has been provided no information with respect to the behavior of single-stranded DNA (or RNA) in hybridization under conditions permitting free conformation of the single-stranded DNA (or RNA).

In the present invention, hybridization with a DNA probe (or RNA probe) is conducted so as to change the conformation of a target DNA (or RNA) into a specific structure to be detected. Accordingly, it is necessary that the DNA (or RNA) in the sample is hybridized under conditions permitting free conformation. On the other hand, in a probe/nucleic acid hybrid molecule which is formed by complementary base-paring upon hybridization of the probe with the nucleic acid molecule in the sample, the hybridized portion has a linear conformation characteristic to its double-stranded chain, while the remainder, i.e., the non-hybridized single-stranded chain has a high-order structure specific to its single-stranded chain, as described above. Accordingly, 3 molecular species can occur; the nucleic acid molecule of double strand (FIG. 1A) not hybridized with the probe (including the nucleic acid molecule failing to hybridize with the probe, thus renatured to the original double strand); the nucleic acid molecule hybridized with the probe (FIG. 1B); and the probe molecule and the nucleic acid molecule in the sample, which are not hybridized thus forming the high-order structure consisting of only a single strand as reported by Orita et al. (FIG. 1C). Significant differences in conformation, structure, and length can be recognized among these molecular species. Hence, by directly observing and distinguishing these differences, it is possible to determine whether a nucleic acid having a sequence hybridized with a probe is present in a sample, and this is one aspect of the present invention. In the present invention, therefore, the nonspecifically bound probe, that is, the probe not bound to the complementary sequence and the probe nonspecifically bound to the substrate plate, can be distinguished on the basis of its conformation and structure from the probe which bound specifically to the complementary sequence, as opposed to the method of using a labeled probe such as the conventional blotting methods where the non-specific binding of the probe can effect a negative influence on detection. Another aspect of the present invention is that the step of amplifying signals from labels, which is required conventionally for detection, can be eliminated so that the time required for probe labeling and washing can be eliminated. Further, as opposed to the conventional blotting methods where the nonspecific binding of the probe has a negative influence on the accuracy of detection, the present invention is characterized in that the nonspecifically bound probe, that is, the probe not bound to the complementary sequence of the target nucleic acid can be distinguished from the probe bound to the complementary sequence on the basis of its conformation and structure.

In the present invention, therefore, the specific binding of the probe is confirmed by directly observing the target nucleic acid molecule hybridized with the probe, so signals of specific binding can be clearly distinguished from noises caused by nonspecific binding, and the problem of detection limit due to noises larger than signals as raised in the conventional methods can thereby be solved. Further, the complicated labeling step and washing step, as well as the time required for such steps, can be eliminated to reduce analysis time.

In the present invention, the nucleic acid probe and the target nucleic acid to be detected are partially hybridized whereby a non-hybridized single-stranded portion is formed in the resulting hybrid nucleic acid, as described above. In cases where a single-stranded portion is generated at the target nucleic acid molecule side, this single-stranded portion has an evidently different structure and size from those of the non-hybridized full-length single-stranded chain, to bring about the advantage for detection in reducing confusion between them. This means that the unique structure and/or size can be controlled by the sequence and length of the nucleic acid probe so that the nucleic acid can be detected rapidly or accurately. On the other hand, in cases where a single-stranded portion occurs at the nucleic acid probe side, the nucleotide sequence of said single-stranded portion can be evidently and completely arbitrary. Accordingly, a nucleotide sequence thereof can be arbitrarily selected to attain a single-stranded portion of a visually prominent shape and/or size, and this contributes to improvements in detection sensitivity. In view of reducing production costs and detection costs, the method of controlling the single-stranded portion (i.e., a part of the target nucleic acid molecule and/or a part of the nucleic acid probe) in the hybrid nucleic acid formed in this manner described above is advantageous, as compared with the conventional methods in which the labeled substance should be increased to improve detection sensitivity. Anyway, according to the present invention, it can be determined whether hybridization between the target nucleic acid molecule and the nucleic acid probe has occurred or not by detecting the hybrid nucleic acid containing both the hybridized linear double-stranded portion and the non-hybridized single-stranded portion which has an unique structure inherent to its nucleotide sequence. When only the hybridized linear double-stranded portion or the non-hybridized single-stranded portion having a unique structure inherent to its sequence is used for evaluation, it is difficult to distinguish them from each other because the forms (FIGS. 1A and 1C) of various nucleic acids present in a sample are very similar. On the other hand, the a hybrid nucleic acid having these two portions is evidently different from other nucleic acid, so that accurate evaluation can be obtained using a combination of said two portions. In particular, the method detecting both the double-stranded region and the single-stranded region is simple and free of detection errors because the whole of the target nucleic acid molecule can be measured as such without cleaving it. Further, if the nucleic acid probe is selected such that the single-stranded region in the resulting hybrid nucleic acid forms a previously known folded high-order structure unique to its nucleotide sequence, it can be confirmed, after detection based on said two regions, whether the detected nucleic acid is the true target nucleic acid or not by measuring the high-order structure of the single-stranded portion in the nucleic acid.

<Procedure of nucleic acid detection>

In one embodiment, the method of detecting nucleic acid according to the present invention consists of the following five steps:

The first step: A sample containing a target nucleic acid molecule having a specific sequence to be detected, and a nucleic acid probe having a complementary sequence to at least a part of the sequence of said nucleic acid molecule, are prepared.

The second step: A reaction solution containing the target nucleic acid molecule and the nucleic acid probe, both in a denatured form, is prepared from the above sample and nucleic acid probe.

The third step: The reaction solution obtained in the second step is renatured to cause the probe and the denatured nucleic acid molecule to hybridize with each other.

The fourth step: The sample obtained in the third step is immobilized onto a substrate plate for scanning probe microscopy.

The fifth step: Imaging the sample obtained in the fourth step under a scanning probe microscope.

Hereinafter, the elements of each step are described in order from the first step.

The sample used in the present invention is not particularly limited insofar as it contains nucleic acid. For example, such nucleic acids are those derived from humor such as blood, saliva, semen, urine, cerebrospinal fluid etc. as well as from organisms such as viruses, microorganisms, fungi, parasites etc. Further, nucleic acids derived from plants etc. can also be essentially used. These nucleic acid molecules can be obtained using conventional isolation and extraction techniques (e.g., U.S. Pat. No. 4,395,486), and the sample is used preferably in the form of a suspension in a suitable buffer. The nucleic acid molecule may be DNA and RNA. The method of preparing a probe to be hybridized with said nucleic acid molecule in the sample is not particularly limited insofar as the probe has a complementary sequence to the target sequence in said nucleic acid molecule. Such probes include those capable of being produced by DNA synthesis techniques. Such method of preparing the probes are known in the art, including, e.g. the techniques described in U.S. Pat. No. 4,734,363. The probe molecule is prepared so as to have a length enough to bind specifically to the nucleic acid molecule to be detected.

From the sample and the probe prepared in this manner, a reaction solution containing the nucleic acid molecule and the nucleic acid probe, both in a denatured form, is prepared. The term "denaturation" used herein refers to treatment for converting double-stranded nucleic acid into single-stranded nucleic acid through heating, alkalization or else. The specific method of preparing a reaction solution containing such denatured nucleic acid molecules is not particularly limited. For example, the sample and the nucleic acid probe may be first mixed and then thermally denatured, or the sample and the nucleic acid probe may be separately thermally denatured and then mixed, whereby their high-order structure are canceled to permit their complementary sequences to hybridize with each other. The manner for increasing the solution temperature to thermally denature the mixed sample is not particularly limited insofar as the high-order structure of the nucleic acid molecule in the sample is canceled to make the molecule single-stranded, and for example, a thermal cycle-controlling unit for PCR, an incubator and so on can be used to enhance the temperature. In addition, a denaturing agent such as alkali, urea, formamide or the like can also be used. Although the time required for thermal denaturation is determined depending on the nucleic acid molecule in the sample and the properties of the probe, suitable conditions can be easily determined by those skilled in the art. Usually, thermal denaturation is carried at a temperature of 60 to 100° C., preferably 100° C. The time required for this thermal denaturation is at least 3 minutes, more preferably 10 minutes.

Briefly summarizing, the second step is a step of canceling the high-order structure of the nucleic acid molecule in the sample and that of the probe to permit complementary sequences to hybridize with each other, and the reaction conditions etc. in this step can be easily selected by those skilled in the art. The present invention is not an invention directed to hybridization, but an invention concerned with observation of the hybridized sample, so that the hybridization method is not particularly limited insofar as the method is known to those skilled in the art and simultaneously meets the conditions described below for the third step.

The third step is the step of renaturing the reaction solution containing the nucleic acid molecule denatured in the second step so that the nucleic acid is hybridized with the probe if its sequence in the sample is complementary to the probe in the mixed sample. The term "renaturing treatment" used herein refers to such a change in the conditions of a reaction solution so as to permit nucleic acids of single strand having complementary sequences contained therein to be converted into double-strand by formation of basepares. Here, it is meant by renaturation that the conditions of the reaction solution are changed such that single-stranded nucleic acids having complementary sequences is rendered double stranded via base-paring. For example, if denaturation in the second step is carried out using heating, the renaturation treatment is to lower the temperature, and if denaturation in the second step is carried out using alkalization, the renaturation treatment is reduction (neutralization). If this renaturation treatment is carried out by decreasing the temperature, the conditions for decreasing temperature (rate of lowering temperature, finally lowered temperature, reaction solution composition etc.) should be determined depending on the target sequence to be detected. However, such conditions would be obvious to those skilled in the art or could be determined as necessary. Usually, hybridization conditions are 30 to 70° C. and 2 to 3 hours. Other conditions for hybridization should be selected such that the structure of the hybridized nucleic molecule can be changed freely. That is, the hybridization in the present method should permit the non-hybridized portion of the nucleic acid molecule to have a high-order structure freely. The prior art relevant to the present invention includes Southern blot hybridization, dot plot hybridization and Northern blot hybridization, as well as in situ hybridization used in the literature of Putman et al. (Putman, C. A. J. et al., Cytometry, 14; 356–361 (1993)). In the in situ hybridization method according to the literature of Putman et al. (supra), a specific probe which has been labeled with diamine benzidine (DAB) via the biotin-avidin reaction is hybridized with a particular sequence in chromosome, so that the specific region in the metaphase chromosome is labeled with a large amount of DAB, and the thickness of amplified DAB is measured under an atomic force microscope. To emphasize the thickness of DAB, DAB concentration and incubation time should be increased. On the other hand, since the metaphase chromosome, as described by Alberts et al. (Molecular Biology of the Cell, 385–406, 1983, Garland Publishing, Inc., New York), forms a molecular structure of a complexly tangled double-stranded chain, its complex cannot be distinguished by merely binding of the probe molecule. Further, in the method of Putman et al., sample cells are previously immobilized onto a slide glass without isolating DNA therefrom to observe them under a microscope. Hence, the molecule of the chromosomal DNA hybridized with the probe cannot take a high-order structure freely. In addition, it is considered that the nonspecific binding cannot be distinguished from the specific binding in this in situ hybridization method, because nonspecific binding if any appears as a change in thickness of the chromosome similar to that due to specific binding. Accordingly, the present invention is considerably and essentially different from the conventional methods in that during hybridization and even after hybridization, the non-hybridized portion of the target nucleic acid can have a high-order structure freely and that, after hybridization, the nonspecifically hybridized probe have a conformation/structure and length different from those of the specifically hybridized probe so that their differences can be detected in the present invention. Furthermore, any of the hybridization methods known in the art other than in situ hybridization also cannot distinguish nonspecific binding from specific binding because the prior hybridization method involves the step of immobilizing the nucleic acid molecule onto carriers such as filter etc. to such a degree that the nucleic acid molecule cannot change its conformation/structure freely. In addition, the PCR method comprises the step of hybridizing DNA in the sample with a DNA probe as a primer and then adding polymerase to elongate its double-stranded chain. Thus, this PCR method does not include the step of the present invention for permitting the single-stranded chain to form a high-order structure.

Finally, the sample hybridized in the third step is immobilized onto a substrate plate for scanning probe microscopy and then observed under a scanning probe microscope. In order to make an image of the sample under the scanning probe microscope after hybridized in the third step, said sample is immobilized onto the substrate plate for scanning probe microscopy. The immobilization method is not particularly limited insofar as the conformation and structure of the molecule to be immobilized are not significantly prevented from changing. In one preferable embodiment, its immobilization onto a mica substrate plate with a smooth surface is carried out using divalent cations. Preferable cations for immobilization are $Mg^{2+}$, and a preferable substrate plate is a mica plate having a cleavage plane on the surface, but with respect to the substrate plate, any plates such as silicon plate, glass plate etc. can be used insofar as they can be used for observation under a scanning probe microscope and permit immobilization of the probe.

Figure 2A:
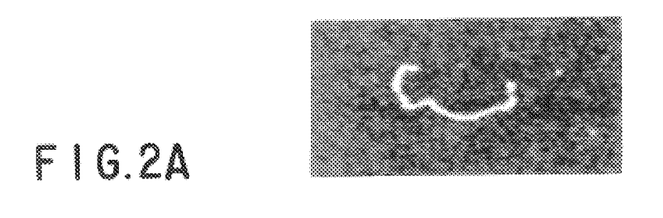
FIGS. 2A to 2C are microphotographs obtained from an atomic force microscope observation, illustrating that a different state of nucleic acid molecule results in a different conformation of the molecule.
Figure 2B:
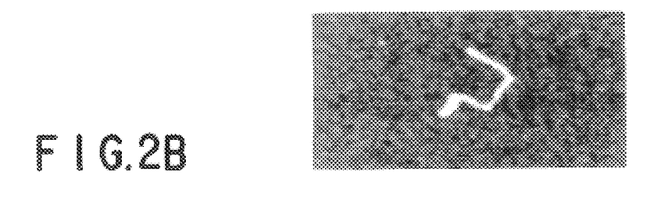
Figure 2C:
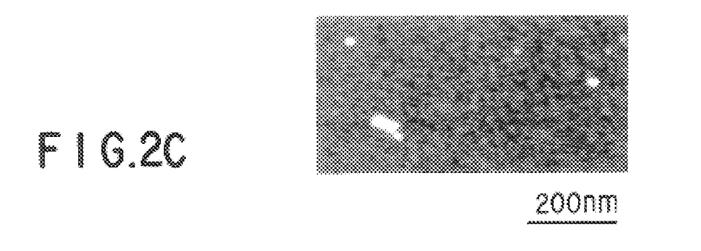

The immobilizing method is specifically as follows; A 10 ml nucleic acid sample at a nucleic acid concentration of 1 to 0.1 µg/ml (10 mM $MgCl_2$, 10 mM HEPES, pH 7.5) is dropped on the cleavage plane of mica, then left for 5 to 10 minutes under wet conditions, washed with pure water, dried in a nitrogen or argon gas and stored in a desiccator at vacuum until observation. An image of the resulting sample under an atomic force microscope is shown in FIGS. 2A to 2C. When the nucleic acid molecules in the sample are double-stranded, the respective molecules are complementary, so the nucleic acid molecules in the sample may hybridize with each other in some cases (FIG. 2A). This may hardly occur depending on hybridization conditions etc. in the second step. The sample nucleic acid molecule hybridized specifically with the probe has a hybridized double-stranded portion and non-hybridized single-stranded portion. Because this single-stranded portion have a globular structure unique to its single-stranded chain, the sample nucleic acid molecule hybridized specifically with the probe is composed of the hybridized linear portion and non-hybridized globular portion (FIG. 2B). The non-hybridized single-stranded probe molecule, and the non-hybridized nucleic acid molecule in the sample, turn globular as a whole (FIG. C). As described in the literature (Rivetti et al., J. Mol. Biol., 264; 919–932, 1996), the probability of the presence of the hybridized nucleic acid molecule in a measurable field on a substrate plate can be increased by amplifying the nucleic acid molecule in the sample by PCR, followed by hybridizing it with an unlabeled nucleic acid probe through the process of the invention. This is different from the conventional PCR method in that it is not necessary to use any probe and that the long time necessary for gel electrophoresis is not required. To make an image of the sample, atomic force microscopes are used as preferable scanning probe microscopes, but apparatuses such as electron microscopes other than the scanning probe microscopes can also be used in consideration of the techniques described in the reference (Thresher et al., J. Mol. Biol. 254; 364–371, 1995). In the latter case, the shape, length etc. of the molecule can roughly be identified. In this case, however, there are many disadvantages, for example, the sample should be observed under vacuum, and the sample should be treated with a metal coating in order to confer electric conductance on it.

As has been described above, according to the present invention, it is possible to determine whether a nucleic acid molecule having a complementary sequence to the probe is present or not, based on an image of a hybrid molecule resulting from hybridization of the DNA molecule with the probe by employing, as criteria, conformation, structure, and length unique to a hybrid molecule. Accordingly, the detection method of the present invention, as compared with the conventional detection methods, is a highly sensitive and accurate detection method at molecular level capable of distinguishing the nonspecific binding from the specific binding of the probe.

In another embodiment, the method for detecting nucleic acid according to the present invention consists of the following 4 steps;

The first step: A probe is immobilized at one end onto a substrate plate for scanning probe microscopy;

The second step: A sample is dropped on and contacted with the probe immobilized on the substrate plate, and then the sample containing the probe and the nucleic acid molecule in the sample is thermally denatured;

The third step: In order to hybridize a nucleic acid having a complementary sequence with the probe, the temperature of the thermally denatured sample of the second step is lowered to permit hybridization of the sequence of said nucleic acid with the probe; and The fourth step: In order to obtain the information on the conformation, structure and length of the hybridized nucleic acid molecule formed in the third step, imaging of the hybridized molecule is performed under a scanning probe microscope.

It is preferable in this embodiment to immobilize the probe nucleic acid molecule onto the substrate plate so as to make sure that the single-stranded portion of the hybridized molecule forms a high-order structure. For example, in the first step, a reactive group such as amino group etc. exposed at one end of the probe nucleic acid molecule is reacted to a reactive group such as amino group etc. which is also exposed on the substrate plate for scanning probe microscopy, thereby forming covalent bounds between them. In other words, if the probe or the nucleic acid molecule in the sample is immobilized onto the substrate plate via its plural sites, the conformation/structure of the molecule is prevented from changing freely, thus making the hybridized portion and non-hybridized portion undistinguishable to deteriorate the advantage of the present invention. The method is specifically as follows;

(i) A mica plate of about 1 cm square (Nisshin EM K.K.) is allowed to stand for 2 hours in vapor of a silane coupling agent having amino groups as functional groups, for example, aminotriethoxy silane from Shin-Etsu Silicone Ltd so as to treat the cleavage plane of the mica plate with the silane coupling agent. The alkoxyl groups (Si—OR) in the silane coupling agent is hydrolyzed to generate silanol groups, which are, in turn, bound onto the mica cleavage plane via condensation reaction, thus attaching exposed amino groups on the mica cleavage plane.

(ii) Then, 20 µl aqueous solution containing 1% glutaraldehyde is added to the mica cleavage plane treated in the manner as described above, then allowed to stand for 5 minutes and washed sufficiently with pure water.

(iii) 20 µl of a suitable DNA probe having an amino coupled to the end thereof (water or 10 mM HEPES buffer, pH 7.5) is dropped on the cleavage plane, and the mica is left at room temperature for 2 hours or stored under shaking to immobilize the DNA probe onto the mica cleavage plane. After this treatment, the mica is washed with pure water to remove the non-immobilized DNA probe.

(iv) In order to block activated amino groups which have not coupled to the DNA prove and are still exposed on the mica cleavage plane, the mica is treated with a solution containing amino groups, such as 10 mM glycine solution or 10 mM Tris solution.

(v) 20 µl sample DNA (10 µg/ml) in 10 mM HEPES buffer is dropped on the mica cleavage plane and kept at 100° C. for 5 minutes.

(vi) The mica substrate plate is placed on a heat block equipped with a Perche element to be cooled rapidly down to 50° C.

(vii) The substrate plate obtained in the above step (vi) is subjected to imaging under an atomic force microscope. For this step, it is preferable that after the step (vi), the substrate plate is washed with 1 to 10 ml pure water and then dried in compressed air, a nitrogen gas or argon gas.

The steps other than immobilization may be essentially the same as in previously described embodiment.

Figure 3A:
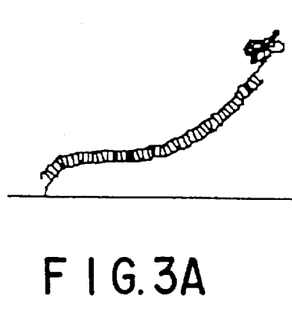
FIGS. 3A to 3C are schematic drawings showing the result of detection of a nucleic acid molecule, where a probe is previously immobilized on a substrate plate and then contacted with a sample for hybridization.
Figure 3B:
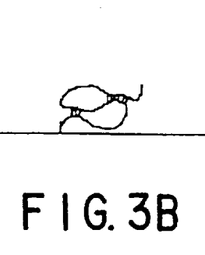
Figure 3C:
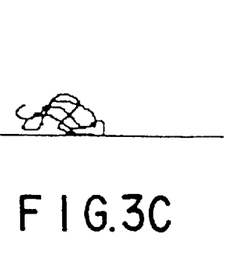

FIGS. 3A to 3C are schematic drawings showing the conformation/structure of a nucleic acid molecule detected in this embodiment of the present invention. FIG. 3A show the hybridized molecule of a probe or DNA in a sample, where the hybridized portion has a linear form characteristic to a double-stranded DNA and the non-hybridized portion has a high-order structure characteristic to a single-stranded DNA. As shown in the Figure, the probe molecule is bound via only its one end to the substrate plate to ensure the formation of the high-order structure of the hybridized molecule. The probe not hybridized with the nucleic acid molecule in the sample, or the sample nucleic acid molecule not hybridized with the probe, is shown FIGS. 3B and 3C, and they have a high-order structure unique to their molecules. Also in the case where the probe molecule has previously been immobilized in this manner, hybridization can be effected to produce high-order structures which can be distinguished from each other under a scanning probe microscope in the same manner as in the above embodiment.

Figure 9:
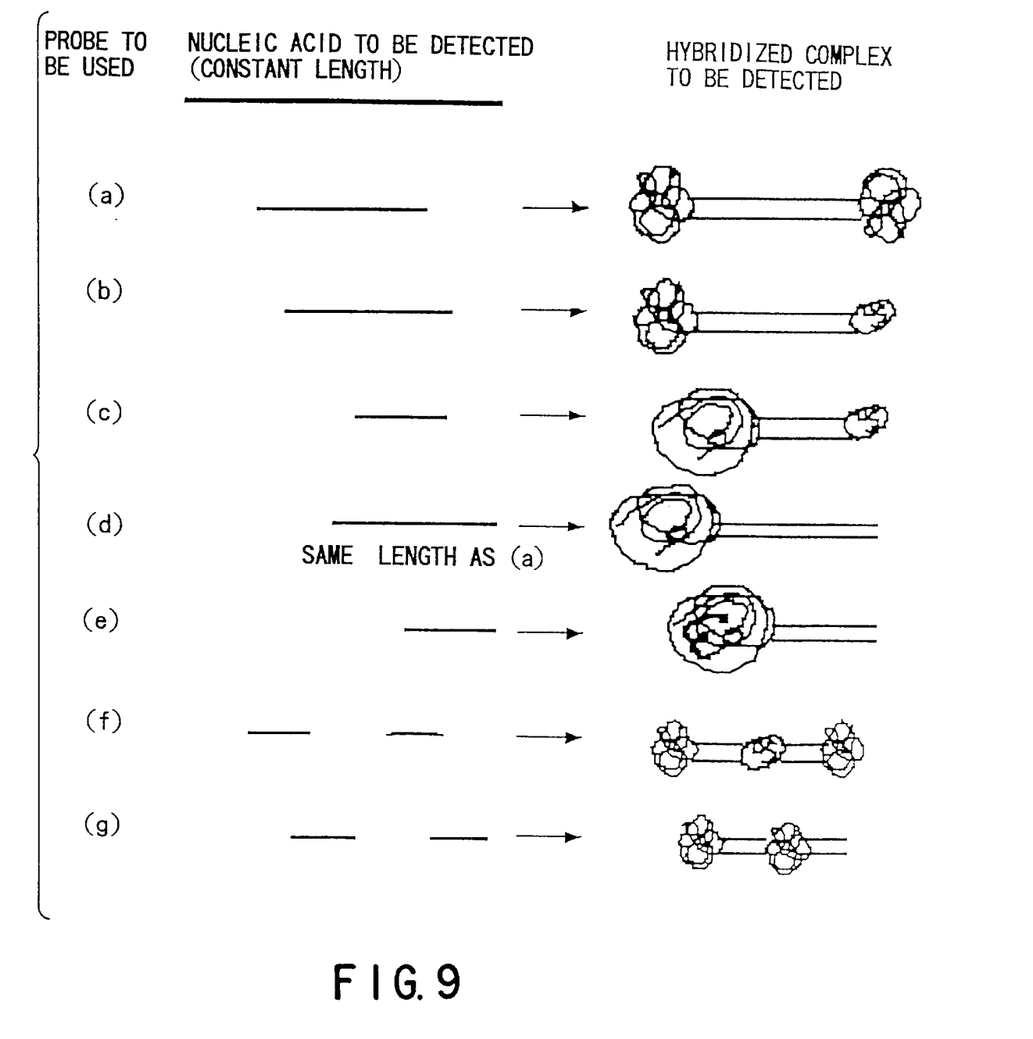

FIG. 9 is a schematic drawing showing differences in the conformation/structure of a hybrid complex formed upon hybridization of different probes with the same nucleic acid molecule. That is, by changing the nucleotide sequence and length of the nucleic acid probe, the target nucleic acid molecule can be imaged as hybrid represening various specific shapes. FIG. 9(a) is an example where a nucleic acid probe shorter by the same distance from both ends of the nucleic acid molecule, is used. FIG. 9(b) shows another example wherein the size of the high-order structure (left side in the Figure) of the nucleic acid molecule are emphasized. In this example, the probe which is longer at the opposite side (right side in the Figure) is used instead of the nucleic acid probe of FIG. 9(a). In FIG. 9(c), the probe shorter at the opposite side (left side in the Figure) to the side to be emphasized is used instead of the nucleic acid probe of FIG. 9(a) in order to emphasize the size of the high-order structure (left side in the Figure) of the nucleic acid molecule. Discrimination similar to FIGS. 9(a), (b) and (c) can be effected even using the number of high-order structures. FIG. 9(d) shows an example where the nucleic acid probe used in FIG. 9(c) is elongated to the end of the nucleic acid molecule (right side in the Figure) at the side opposite to the high-order structure, in order to form only one high-order structure and the linear nucleic acid portion of FIG. 9(c). In FIG. 9(e), the length of the nucleic acid probe used in FIG. 9(d) is shortened on the high-order structure side (left side in the Figure) at the maximum degree within the allowable range for distinguishing the linear portion, in order to more emphasize the high-order structure by further shortening the linear portion of FIG. 9(d). FIGS. 9(f) and 9(g) are examples where the nucleic acid probe is divided for use. In FIG. 9(f), use is made of the same nucleic acid probe having the same sequence as in FIG. 9(a) except that the probe has two fragments separated by an cut-off portion having a length capable of forming the high-order structure so that each portion can be emphasized. In this case, hybrid formed by hybridization has three high-order structures (that is, 2 high-order structures at both ends and 1 high-order structure in a central portion) and/or two linear portions, and hence, the hybrid can be easily distinguished based on this criteria. In FIG. 9(g), the position of the nucleic acid probe to be hybridized with the target nucleic acid molecule is shifted to the end (right side in the Figure) such that only one end in FIG. 9(f) (left side in the Figure) has a high-order structure and the other end becomes linear, as in the case of FIG. 9(d) and FIG. 9(e). In this case, the hybrid has 2 high-order structures (that is, 1 high-order structure at one end and 1 high-order structure in a central portion) and/or 2 linear portions, and then, this hybrid can be easily distinguished based on these criteria. As described above, when the nucleic acid probe divided into two fragments prepared by removing a nucleotide sequence of suitable size is used, it is possible to form a unique shape having a high-order structure of suitable size between linear portions. Here, the number of the probe fragments thus divided can be 3 or more to increase diversity. In addition, when the nucleic acid probe fragments thus divided are prepared such that their nucleotide sequences bind respectively to both ends of the target nucleic acid molecule, 1 or more high-order structures can be formed in only central portions of the nucleic acid molecule. In this manner, by suitably varying and combining nucleotide sequences and/or lengths of the nucleic acid probe so that various shapes of the nucleic acid molecule/ nucleic acid probe hybrid complex, not only one but also plurality of nucleic molecules can be distinguished simultaneously or separately.

In the combination of FIGS. 9 (a) to (e) above, the probe is shorter than the nucleic acid to be detected. However, the nucleic acid probe may be longer than the nucleic acid to be detected. In this case, the region rendered single-stranded after hybridization is a part of the nucleic acid probe. Accordingly, the nucleotide sequence of the region rendered single-stranded in the nucleic acid probe can be arbitrarily selected. When the region rendered single-stranded in the nucleic acid probe is longer, a larger globular structure is formed, so that the hybrid molecule can be detected even under a microscope with lower magnification without any limit to the length of the nucleic acid molecule to be detected. In addition, a nucleic acid probe having a nucleotide sequence which forms a high-order structure (e.g., 8-shaped, zigzag, spiral, star-shaped, etc.) capable of being easily distinguished is used, it is possible to detect a target nucleic acid molecule by using the shape of its single-stranded portion independent of the nucleotide sequence of the target molecule. Further, even in cases where a plurality of nucleic acid probes are used for detect a plurality of nucleic acid molecules, the presence and type of a target nucleic acid molecule can be judged by comparing only the size (e.g., average diameter) of the single-stranded region in the hybrid molecule when the nucleotide sequence of said region in the probe is selected such that the regions rendered single-stranded upon hybridization are the same in shape but different in size.

Further, even if the target nucleic acid molecule and the nucleic acid probe molecule are the same in length, they can be applied to the present invention in the same manner as described above insofar as the single-stranded chain after hybridization forms a high-order structure. For example, if the nucleotide sequence of the nucleic acid probe is complementary to the target nucleic acid molecule in only a central part thereof, a double-stranded chain forms in only the complementary portion, and single-stranded high-order structures are formed at both ends respectively. As a result, also in this case, the hybridized nucleic acid can be detected according to the present invention since the hybridized central double-stranded portion and the terminal single-stranded portions are formed.

Further, in the case where the nucleic acid probe is shorter than the target nucleic acid molecule to be detected, only a part of the nucleic acid probe may form base-pairs with the nucleic acid molecule. Similarly, in the case where the nucleic acid probe is longer than the nucleic acid molecule, only a part of the nucleic acid molecule may form base-pairs with the nucleic acid probe.

EXAMPLES

Example 1

Relationship between the state and shape of DNA

<Experimental Procedures>

(i) DNA having the sequences shown in SEQ ID NOS: 1 and 2 were used. The terminal 751 base-pairs of DNA in SEQ ID NO: 1 is in common with those of the sequence of SEQ ID NO: 2. First, plasmid pGEX-PH (with a prextrin domain inserted into a BamHI-EcoRI site in plasmid pGEX-3X available from Pharmacia) was digested with restriction enzymes HincII or HicII and BamHI at 37° C. to give 1830-bp and 751-bp DNA fragments respectively.

(ii) The above cleaved DNA were mixed at the ratio of 1:1 in a buffer (1 mM EDTA, 10 mM Tris-HCl, pH 8.0), then denatured by heating at 100° C. for 10 minutes, and hybridized at 50° C. for 2 hours. This nucleic acid sample was diluted to 0.1 $\mu$g/ml with 10 mM $MgCl_2$ in 10 mM HEPES (pH 7.5), dropped on a square mica base plate of about 1 cm in one side and left for 30 minutes at room temperature under wet conditions, and the base plate was washed with pure water and dried in an argon gas.

(iii) An image was made of the sample thus prepared under an atomic force microscope.

<Experimental Results>

FIG. 2A shows the sample DNA (the sample of SEQ ID NO:2) renatured into the original double-stranded chain by hybridization. FIG. 2B shows the DNA of SEQ ID NO:2 hybridized with the DNA of SEQ ID NO:1. This molecule has a double-stranded portion hybridized specifically with the probe and a single-stranded portion not hybridized. And the non-hybridized DNA molecule becomes globular as a whole (FIG. 2C).

<Discussion>

As can be seen from the above results, the double-stranded portion and the single-stranded portion are different from each other in high-order structure. Therefore, specific hybridization with the probe can be proven by detection of the linear double-stranded chain.

Example 2

Proof that a single-stranded DNA has a different high-order structure depending on its sequence and the length of a probe <Experimental Procedures>

(i) First, plasmid pUC118 was linearized by digestion with restriction enzyme EcoRI. Plasmid pUC118 is available as a suspension in buffer from e.g. Takara Shuzo Co., Ltd. Alternatively, pUC118 can be obtained by transforming *E. coli* (e.g. JM109 available from Takara Shuzo Co., Ltd.) with pUC118, then recovering said plasmid from the transformed *E. coli* and purifying it by ion chromatography (e.g. QIAGEN Plasmid Kit from QIAGEN GmbH). Plasmid pUC118 is a cyclic DNA with a multicloning site containing one EcoRI restriction enzyme site. Plasmid pUC118 is then cleaved at the EcoRI site by digesting it at 37° C. with 5 units/$\mu$g of restriction enzyme EcoRI (commercially available from Toyobo Co., Ltd.) whereby 3.2 kbp linear DNA was obtained.

(ii) Then, 5 $\mu$g of the linear DNA obtained above was reacted at 25° C. with 150 U exonuclease III (commercially available from Toyobo Co., Ltd.). This reaction was conducted in 25 $\mu$l of 50 mM Tris-HCl (pH 7.6), 1 mM $MgCl_2$, 1 mM 2-mercaptoethanol. The reaction time was 0 minute, 5 minutes, 10 minutes or 15 minutes.

Figure 4A:
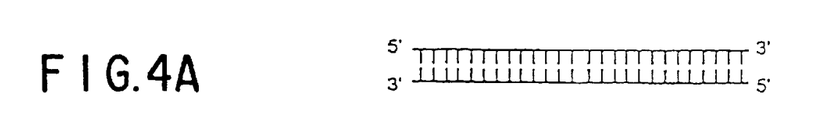
FIGS. 4A to 4C are drawings showing a preliminary experiment conducted to show the principle of the method of the present invention.
Figure 4B:
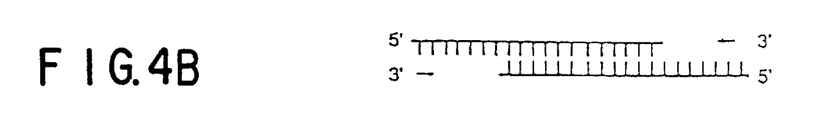
Figure 4C:
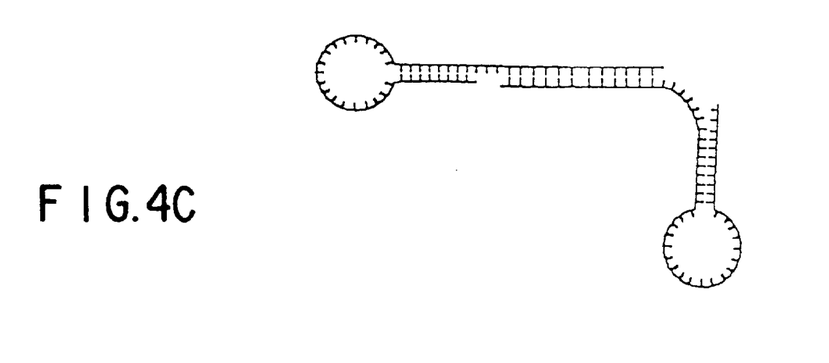

FIGS. 4A to 4C shows a schematic drawing showing the changes of linear pUC118 formed by this reaction. In this drawing, FIG. 4A shows the double-stranded DNA before the reaction. If exonuclease III is allowed to act on this double-stranded DNA, the nucleotide is cleaved off in order from the 3'-sides of DNA chains to yield single-stranded DNA at both ends. The single-stranded portion of one chain is a sense chain, and the single-stranded portion of the other is an antisense chain. The respective single-stranded portions thus formed are base-paired mutually to form the high-order structure shown in FIG. 4C.

It was confirmed in the following manner that the reaction shown in FIGS. 4A to 4C has occurred. That is, the above reaction product was reacted with S1 nuclease at 23° C. for 15 minutes. Only the single-stranded portion is thereby digested so that DNA consisting of only the double-stranded chain which is shorter than the originally double-stranded chain is obtained. Then, the DNA is subjected to agarose gel electrophoresis and visualized by staining with ethidium bromide. If a smaller double-stranded DNA than the original double-stranded DNA is detected according to the degree of emigration of its detected band, it can be confirmed that the above exonuclease reaction has occurred.

(iii) Each DNA chain obtained by the above reaction with exonuclease III was measured using atomic force microscopy (AFM). For measurement, the DNA partially digested in the above step (ii) was diluted at a concentration of about 0.01 μg/ml in 10 mM HEPES buffer, 10 mM $MgCl_2$. 10 μl of this DNA diluted solution was dropped on a cleavage plane of mica (mica plate of about 1 cm×1 cm with any arbitrary shape) and left for 30 minutes whereby the DNA molecule was adsorbed onto the mica cleavage plane. It was washed with about 1 ml pure water, dried in an inert gas atmosphere such as Ar or $N_2$ and then measured by AFM. The AFM microscope used was Nanoscope IIIa commercially available from Digital Instrument Ltd., Santa Barbara, Calif., USA.

To prepare the above DNA diluted solution, a buffer other than HEPES may also be used, and other divalent cations may be used in place of Mg. The time during which the sample is left for adsorption of the DNA onto the mica cleavage plane is determined depending on the concentration of the DNA diluted solution. For the method of adsorbing the DNA onto the mica cleavage plane, see e.g. Helen G. Hansma, et al. Nucleic Acids Research 1996, Vol. 24, No. 4.

<Experimental Results>

Figure 5:
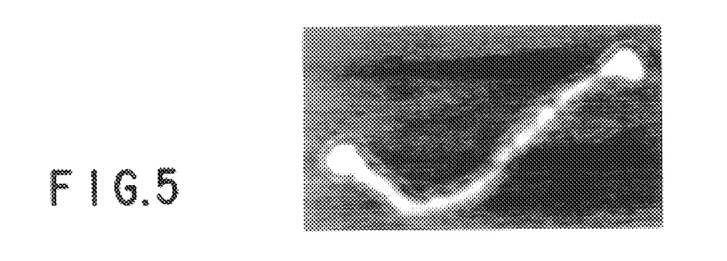
FIG. 5 is a microphotograph in AFM of a DNA molecule in the state shown in FIG. 4C.
Figure 6:
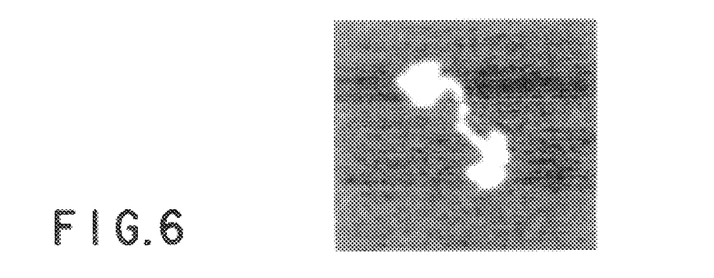
FIG. 6 is a microphotograph in AFM of another DNA molecule in the state shown in FIG. 4C, with a shorter double-stranded portion than in FIG. 5.

The measurement results in (ii) above were as follows:

FIG. 5 shows the measurement result of the DNA sample which was reacted with exonuclease III for 10 minutes. FIG. 6 shows the measurement result of the DNA sample where the reaction time was 15 minutes. These indicate that single-stranded high-order structures are present at the ends of the linear double-stranded portion. Further, the high-order structures present at both ends are different from each other depending their respective nucleotide sequences. From comparison between FIGS. 5 and 6, it can be seen that as the reaction proceeds, the central portion of the double-stranded chain is shortened and the high-order structures at both ends become larger, and the high-order structures themselves at both ends are changed. In the case where the reaction time was 5 minutes, the central linear portion was longer than in FIG. 5, while the high-order structural portions at both ends were smaller than in FIG. 5 (see FIG. 7).

Figure 7:
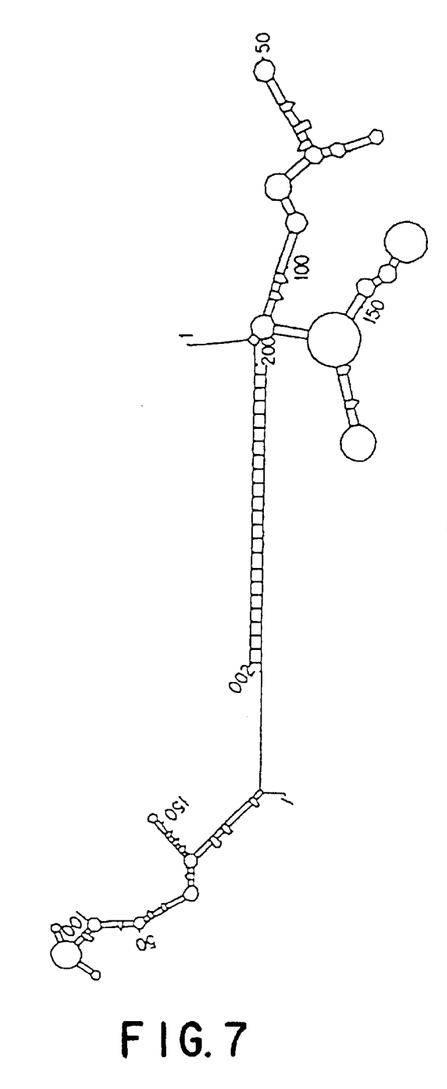
FIG. 7 is a drawing of the DNA molecule structure obtained by computer analysis of the information which is obtained from AFM measurement of the DNA molecule in the state shown in FIG. 4C.

FIG. 7 shows the result of analysis of the DNA sample (AFM photograph was omitted) by commercial computer software, which was obtained using the measurement results in AFM. From this drawing, it is understood that high-order structures have already been formed at both ends of the DNA molecule rendered single-stranded and the respective high-order structures are different from each other depending on the difference of their nucleotide sequences. The numbers in the drawing indicate the nucleotide numbers of the DNA sample.

Figure 8:
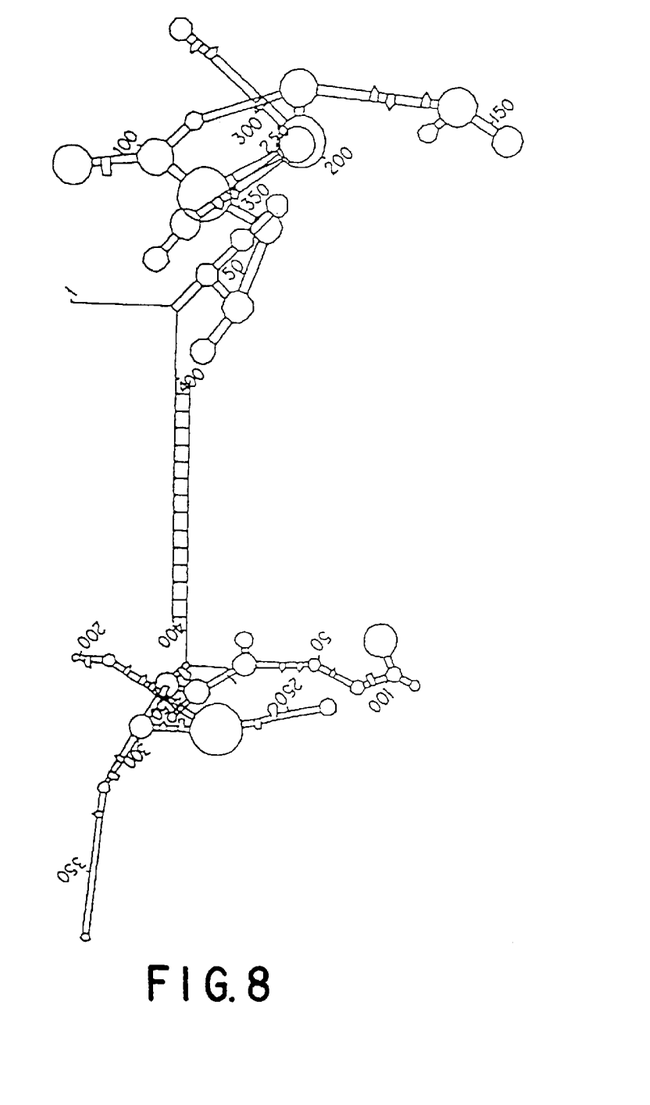
FIG. 8 is a drawing of the DNA molecule structure obtained by computer analysis of the information which is contained in the AFM microphotograph shown in FIG. 5.

FIG. 8 shows the analysis result of the photograph in AFM (reaction time: 10 minutes) by use of the same computer software as above. In this analysis result, the difference of the high-order structures present at both ends of the double-stranded portion is shown more clearly than in the photograph of FIG. 5. The respective high-order structures and the size of the linear portion, as well as the nucleotide numbers, are shown in the drawing.

When the same enzyme reaction was continued for 20 minutes, the whole molecule was rendered single-stranded and there was no change even after further reaction.

<Discussion>

As can be seen from the above results, the high-order structure of each single-stranded DNA is varied clearly depending on its nucleotide sequence. Further, the double-stranded portion is evidently different from the high-order structure of the single-stranded portion. Accordingly, by detection of the linear double-stranded chain, specific hybridization with the probe can be proven, and it is also possible to obtain the information on the portion where it was not hybridized. Further, the shape of a probe/nucleic acid molecule complex and the dimension in high-order structure of the single-stranded DNA can be made distinguishable by suitably changing the sequence and length of the probe, so the data base necessary for the step of identifying the nucleic acid to be detected can be made small-scale and detection results can be obtained easily and rapidly.

Example 3

A method of immobilizing a probe, and detection of a nucleic acid molecule by use of the immobilized probe <Experimental Procedures>

(i) A cleavage plane of square mica of about 1 cm in one side (Nisshin EM K.K.) was left for 2 hours in vapor of a silane coupling agent having amino groups as functional groups (aminopropyl triethoxy silane available from Shin-Etsu Silicone Co., Ltd.).

(ii) Then, 20 μl of an aqueous solution containing 1% glutaraldehyde was added to the mica cleavage plane treated in the manner as described above, then allowed to stand for 5 minutes and washed sufficiently with pure water.

(iii) 20 μl of the DNA probe (SEQ ID NO:2) having an amino group added to the end thereof (water or 10 mM HEPES buffer, pH 7.5, 1 mM EDTA) was dropped on the mica, and the mica was left at room temperature for 2 hours to immobilize the DNA probe onto the mica cleavage plane. After this treatment, it was washed with pure water to remove the non-immobilized DNA probe.

(iv) The mica base plate was treated with 10 mM glycine solution.

(v) 20 μl of the sample DNA (10 μg/ml) in 10 mM HEPES buffer, pH 7.5, 10 mM $MgCl_2$ was dropped on the DNA probe immobilized on the mica cleavage plane and kept at 100° C. for 5 minutes.

(vi) The mica base plate was placed and cooled rapidly to 50° C. on a heat block using a Perche element, and then the base plate was washed with about 10 ml pure water and dried in an argon gas.

(vii) An image was made of the base plate obtained in the above step (vi) by atomic force microscopy.

<Experimental Results>

The structure of the nucleic acid molecule to be detected in this example was essentially the same as in the schematic drawings in FIGS. 3A to 3C.

The effects achieved by the method for detecting nucleic acid according to the present invention are as follows:

Labeling of a sample with a probe molecule for detection can be eliminated essentially:

The operation of lowering noises caused by the nonspecific binding of the probe at the time of detection can be eliminated essentially.

Detection can be feasible in principle even if the sample contains only one target molecule.

Because the molecule is directly observed, detection can be feasible even using a trace amount of a sample.

---

What is claimed is:

1. A method for detecting a target nucleic acid molecule hybridized with a nucleic acid probe, comprising:
    (a) hybridizing a target nucleic acid molecule having a specific sequence to be detected in a sample with a nucleic acid probe having a sequence complementary to the specific sequence of the target nucleic acid molecule, said nucleic acid probe being such that the target nucleic acid molecule and the nucleic acid probe are partially hybridized to represent a linear conformation in a hybridized region and to represent, in a non-hybridized region, a unique structure inherent to its nucleotide sequence;
    (b) measuring the size of the target nucleic acid molecule in step (a), wherein the measuring measures an average diameter of the unique structure under microscope observation; and
    (c) on the basis of the resultant measurement data obtained in step (b), detecting a nucleic acid containing both of said linear conformation and said unique structure, thereby detecting said target nucleic acid molecule hybridized with said nucleic acid probe.

2. A method according to claim 1, wherein the non-hybridized region has a folded shape unique to its nucleotide sequence.

3. A method according to claim 1, wherein the non-hybridized region is globular-like.

4. A method according to claim 1, wherein the nucleic acid probe comprises two or more probes having complementary sequences to sequences of different portions in the target nucleic acid molecule to be detected.

5. A method according to claim 1, wherein the measuring in step (b) measures a solution containing the hybridized nucleic acid molecule on a flat surface.

6. A method according to claim 1, wherein the measuring in step (b) measures a solution containing the hybridized nucleic acid molecule.

7. A method for detecting different target nucleic acid molecules by using different nucleic acid probes, comprising:
- (a) hybridizing different target nucleic acid molecules to be detected with different nucleic acid probes, said different nucleic acid probes being such that each of said nucleic acid probes and one of said target nucleic acid molecules are partially hybridized to represent a linear conformation in a hybridized region and to represent, in a non-hybridized region of said nucleic acid probe, a unique structure inherent to its nucleotide sequence;
- (b) measuring the size of the target nucleic acid molecules obtained in step (a), wherein the measuring measures an average diameter of the unique structure under microscope observation; and
- (c) on the basis of the resultant measurement data obtained in step (b), determining the size of the unique structure, thereby selectively detecting the target nucleic acid molecules hybridized with the corresponding nucleic acid probes, wherein said different nucleic acid probes have respective regions comprising unique nucleotide sequences not hybridizing with their target nucleic acid molecule, said unique nucleotide sequences of said different nucleic acid probes being different from each other depending on the corresponding target nucleic acid molecules to be detected.

8. A method according to claim 7, wherein said unique nucleotide sequences of said different nucleic acid probes are such that the respective unique structures are common in shape, but different in size.

9. A method according to claim 7, wherein the measuring in step (b) measures a solution containing the hybridized nucleic acid molecule on a flat surface.

10. A method according to claim 1, wherein the hybridizing in step (a) further comprises immobilizing the nucleic acid probe onto a base plate.

11. A method according to claim 7, wherein the hybridizing in step (a) further comprises immobilizing the nucleic acid probe onto a base plate.

12. A method according to claim 1, wherein the measuring in step (b) includes imaging under a microscope.

13. A method according to claim 12, wherein the imaging is carried out by measurement of an image by scanning probe microscopy.

14. A method according to claim 7, wherein the measuring in step (b) includes imaging under a microscope.

15. A method according to claim 14 wherein the imaging is carried out by measurement of an image by scanning probe microscopy.

16. A method according to claim 1, wherein the measuring in step (b) measures the solution containing the hybridized nucleic acid molecule.

17. A method according to claim 7, wherein the measuring in step (b) measures the solution containing the hybridized nucleic acid molecule.

18. A method according to claim 1, wherein the nucleic acid probe is a DNA.

19. A method according to claim 7, wherein the nucleic acid probe is a DNA.

20. A method according to claim 1, wherein the nucleic acid probe is a RNA.

21. A method according to claim 7, wherein the nucleic acid probes comprise RNA probes.

22. A method according to claim 1, wherein the target nucleic acid molecule is a DNA.

23. A method according to claim 7, wherein the target nucleic acid molecules comprise DNA.

24. A method according to claim 1, wherein the target nucleic acid molecule is a RNA.

25. A method according to claim 7, wherein the target nucleic acid molecules comprise RNA.

* * * * *

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 751
      (B) TYPE: nucleic acid
      (C) STRANDEDNESS: double
      (D) TOPOLOGY: linear    (ii) MOLECULE TYPE: other nucleic acid    (vii) IMMEDIATE SOURCE:
      (A) LIBRARY: pGEX-PH    (xi) SEQUENCE DESCRIPTION: SEQ ID NO:1:

```
GACAATTAAT CATCGGCTCG TATAATGTGT GGAATTGTGA GCGGATAACA ATTTCACACA      60
GGAAACAGTA TTCATGTCCC CTATACTAGG TTATTGGAAA ATTAAGGGCC TTGTGCAACC     120
CACTCGACTT CTTTTGGAAT ATCTTGAAGA AAAATATGAA GAGCATTTGT ATGAGCGCGA     180
TGAAGGTGAT AAATGGCGAA ACAAAAAGTT TGAATTGGGT TTGGAGTTTC CCAATCTTCC     240
TTATTATATT GATGGTGATG TTAAATTAAC ACAGTCTATG GCCATCATAC GTTATATAGC     300
TGACAAGCAC AACATGTTGG GTGGTTGTCC AAAAGAGCGT GCAGAGATTT CAATGCTTGA     360
AGGAGCGGTT TTGGATATTA GATACGGTGT TTCGAGAATT GCATATAGTA AAGACTTTGA     420
AACTCTCAAA GTTGATTTTC TTAGCAAGCT ACCTGAAATG CTGAAAATGT TCGAAGATCG     480
TTTATGTCAT AAAACATATT TAAATGGTGA TCATGTAACC CATCCTGACT TCATGTTGTA     540
TGACGCTCTT GATGTTGTTT TATACATGGA CCCAATGTGC CTGGATGCGT TCCCAAAATT     600
AGTTTGTTTT AAAAAACGTA TTGAAGCTAT CCCACAAATT GATAAGTACT TGAAATCCAG     660
CAAGTATATA GCATGGCCTT TGCAGGGCTG GCAAGCCACG TTTGGTGGTG GCGACCATCC     720
TCCAAAATCG GATCTGATCG AAGGTCGTGG G                                    751
```

(2) INFORMATION FOR SEQ ID NO:2:

(i) SEQUENCE CHARACTERISTICS:
      (A) LENGTH: 1830
      (B) TYPE: nucleic acid
      (C) STRANDEDNESS: double
      (D) TOPOLOGY: linear    (ii) MOLECULE TYPE: other nucleic acid    (vii) IMMEDIATE SOURCE:
      (A) LIBRARY: pGEX-PH    (xi) SEQUENCE DESCRIPTION: SEQ ID NO:2:

```
GACAATTAAT CATCGGCTCG TATAATGTGT GGAATTGTGA GCGGATAACA ATTTCACACA      60
GGAAACAGTA TTCATGTCCC CTATACTAGG TTATTGGAAA ATTAAGGGCC TTGTGCAACC     120
CACTCGACTT CTTTTGGAAT ATCTTGAAGA AAAATATGAA GAGCATTTGT ATGAGCGCGA     180
```

-continued

```
TGAAGGTGAT AAATGGCGAA ACAAAAAGTT TGAATTGGGT TTGGAGTTTC CCAATCTTCC    240

TTATTATATT GATGGTGATG TTAAATTAAC ACAGTCTATG GCCATCATAC GTTATATAGC    300

TGACAAGCAC AACATGTTGG GTGGTTGTCC AAAAGAGCGT GCAGAGATTT CAATGCTTGA    360

AGGAGCGGTT TTGGATATTA GATACGGTGT TTCGAGAATT GCATATAGTA AAGACTTTGA    420

AACTCTCAAA GTTGATTTTC TTAGCAAGCT ACCTGAAATG CTGAAAATGT TCGAAGATCG    480

TTTATGTCAT AAAACATATT TAAATGGTGA TCATGTAACC CATCCTGACT TCATGTTGTA    540

TGACGCTCTT GATGTTGTTT TATACATGGA CCCAATGTGC CTGGATGCGT TCCCAAAATT    600

AGTTTGTTTT AAAAAACGTA TTGAAGCTAT CCCACAAATT GATAAGTACT TGAAATCCAG    660

CAAGTATATA GCATGGCCTT TGCAGGGCTG GCAAGCCACG TTTGGTGGTG GCGACCATCC    720

TCCAAAATCG GATCTGATCG AAGGTCGTGG GATCCATGGC TGCAGTGATA CTGGAGAGCA    780

TCTTTCTGAA GCGCTCCCAG CAGAAAAAGA AAACATCACC TTTAAACTTC AAGAAGCGCC    840

TGTTTCTCTT GACTGTACAC AAACTTTCAT ACTATGAATA TGACTTTGAA CGTGGGAGAA    900

GAGGCAGTAA GAAAGGTTCA ATAGATGTTG AGAAGATCAC CTGTGTTGAA ACAGTAATTC    960

CTGAAAAAAA TCCCCCACCA GAAAGACAGA TTCCGAGGAG AGGTGAGGAG TCTAGTGAAA   1020

TGGAACAGAT TTCAATCATT GAAAGGTTCC CGTACCCATT CCAGGTTGTA TATGATGAAG   1080

GACCTCTCTA TGTTTTCTCC CCAACTGAAG AGCTGAGAAA GCCGTGGATT CACCAGCTCA   1140

AAAATGTAAT CCGGTACAAT AGTGACCTGA ATTCATCGTG ACTGACTGAC GATCTGCCTC   1200

GCGCGTTTCG GTGATGACGG TGAAAACCTC TGACACATGC AGCTCCCGGA GACGGTCACA   1260

GCTTGTCTGT AAGCGGATGC CGGGAGCAGA CAAGCCCGTC AGGGCGCGTC AGCGGGTGTT   1320

GGCGGGTGTC GGGGCGCAGC CATGACCCAG TCACGTAGCG ATAGCGGAGT GTATAATTCT   1380

TGAAGACGAA AGGGCCTCGT GATACGCCTA TTTTTATAGG TTAATGTCAT GATAATAATG   1440

GTTTCTTAGA CGTCAGGTGG CACTTTTCGG GGAAATGTGC GCGGAACCCC TATTTGTTTA   1500

TTTTTCTAAA TACATTCAAA TATGTATCCG CTCATGAGAC AATAACCCTG ATAAATGCTT   1560

CAATAATATT GAAAAAGGAA GAGTATGAGT ATTCAACATT TCCGTGTCGC CCTTATTCCC   1620

TTTTTTGCGG CATTTTGCCT TCCTGTTTTT GCTCACCCAG AAACGCTGGT GAAAGTAAAA   1680

GATGCTGAAG ATCAGTTGGG TGCACGAGTG GGTTACATCG AACTGGATCT CAACAGCGGT   1740

AAGATCCTTG AGAGTTTTCG CCCCGAAGAA CGTTTTCCAA TGATGAGCAC TTTTAAAGTT   1800

CTGCTATGTG GCGCGGTATT ATCCCGTGTT                                   1830
```